United States Patent [19]

Cool

[11] Patent Number: 4,657,872
[45] Date of Patent: Apr. 14, 1987

[54] LASER-ENHANCED FLAME IONIZATION DETECTION

[75] Inventor: Terrill A. Cool, Trumansburg, N.Y.

[73] Assignee: Cornell Research Foundation, Inc., Ithaca, N.Y.

[21] Appl. No.: 670,798

[22] Filed: Nov. 13, 1984

[51] Int. Cl.[4] .......................................... G01N 27/62
[52] U.S. Cl. ............................... 436/154; 204/157.61; 422/54
[58] Field of Search ....... 204/162 R, 162 HE, 157.61; 436/153, 154, 35; 422/54

[56] References Cited

U.S. PATENT DOCUMENTS 4,012,301 3/1977 Rich et al. .................. 204/162 R X

OTHER PUBLICATIONS

Turk, et al., Analytical Chemistry, vol. 54, No. 9, Aug. 1982, pp. 1006A–1018A.
Travis et al., Analytical Chemistry, vol. 51, No. 9, Aug. 1979, pp. 1516–1520.
Turk et al., Analytical Chemistry, vol. 50, No. 6, May 1978, pp. 817–820.
Cool et al., Chemical Abstracts, vol. 102, 1985, No. 102:9096t.
Butler et al., Chemical Abstracts, vol. 93, 1980, No. 93:174509h.
Shaub et al., Chemical Abstracts, vol. 93, 1980, No. 93:174510b.
Nokes et al., Chemical Abstracts, vol. 100, 1984, No. 100:22292g.
Zavitsanos et al., Chemical Abstracts, vol. 68, 1968, No. 7831j.
Cool et al., Chem. Phys. Lett., III: 82 (1984).
Cool, Applied Optics, 23: 1559 (1984).
Brzozowski et al., The Astrophysical Jrnl, 207: 414 (1976).
Peeters et al., 15th Symposium of Combustion: 969 (1975).
Fontijn et al., 10th Symposium of Combustion: 545 (1965).
Peeters et al., 12th Symposium on Combustion: 437 (1969).
Miller, 14th Symposium of Combustion: 307 (1973).
Calcote, Combustion and Flame, 42: 215 (1981).
Peeters et al., 14th Symposium on Combustion: 133 (1973).
Nokes et al., Chem. Phys. Letters, 99: 491 (1983).
Bonczyk et al., Combustion and Flame, 34: 253 (1979).
Cottereau et al., Am. Chem. Soc. Symposium Series 134: 131 (1980).
Travis et al., J. Chem. Educ. 59, 909, (1982).
Turk et al., Anal. Chem. 51, 1890 (1979).

Primary Examiner—Arnold Turk
Attorney, Agent, or Firm—Jones, Tullar & Cooper

[57] ABSTRACT

A pulsed or discontinuous laser-enhanced flame ionization detector for detection of traces of hydrocarbons in gaseous samples. The use of a laser in conjunction with flame ionization significantly increases the ratio of electronically excited CH radicals to ground electronic state CH radicals thereby increasing the signal to noise ratio during measurement, thus increasing the sensitivity of the flame ionization detection method.

7 Claims, 5 Drawing Figures

LASER-ENHANCED FLAME IONIZATION DETECTION

The present invention resulted in part from research sponsored by the National Science Foundation under Grant No. CPE 81-19408. The United States Government may have rights under this invention.

BACKGROUND OF THE INVENTION

Flame ionization detectors are known in the art and are frequently employed to further analyze a sample which is an effluent of a gas chromatograph. A review of the operating characteristics of flame ionization detectors by Blades is found at *J. Chromatographic Science*, 11: 251-255 (May 1973).

Flame ionization detectors presently used for the detection of traces of hydrocarbons (i.e. organic compounds containing CH groups) in gaseous samples are based on chemi-ionization reactions which occur when a hydrocarbon is introduced within a hydrogen/oxygen or hydrogen/air flame [McWilliam et al, *Gas Chromatography*, 1958, (Desty et al., ed.) Academic Press, N.Y., 1958, pp. 142-145; Perry, Introduction to Analytical Gas Chromatography, Marcel Dekker, Inc., N.Y., 1981, pp. 156-177; Littlewood, *Gas Chromatography, Principles, Techniques and Applications*, Academic Press, N.Y., 1970, pp. 301-307; Bruderreck et al., J. Chromatog., 1964, 36: 461-473]. The primary reaction thought to be responsible for this chemi-ionization is that between the CH radical and 0 atoms [Calcote, *Combust. Flame*, 1957, 1: 385, i.e., $$CH(X^2\pi) + 0 \rightarrow HCO^+ + e^-. \quad (1)$$

Present hydrocarbon detection methods are based upon measurement of the ionization current drawn from the flame by electrodes polarized by external circuitry. Ionization detection efficiencies approaching $n_c \times 10^{-4}$ electrons detected per hydrocarbon molecule, where n is the number of carbon atoms in the molecule, are possible with currently available flame ionization detectors.

In my laboratory it was recently found that the chemi-ionization reactions $$CH(A^2\Delta, B^2\Sigma^-) + 0 \rightarrow HCO^+ + e^- \quad (2)$$

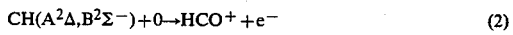

have rate constants, under flame conditions, which are approximately 2000 times faster than that previously determined [Peeters et al., 15th Symposium (Internat.) on Combustion, the Combustion Inst., 1975, pp. 696.] for the chemi-ionization reaction (1). Laser absorption methods can be used to convert ground electronic state $CH(X^2\pi)$ radicals to electronically excited $CH(A^2\Delta, B^2\Sigma^-)$ radicals so that chemi-ionization can proceed at a vastly accelerated rate via reaction (2) compared with the chemi-ionization rate associated with reaction (1). This laser-induced enhancement of chemi-ionization provides the basis for a new type of flame ionization detector described herein.

DESCRIPTION OF THE INVENTION

This invention relates to a pulsed or discontinuous laser-enhanced flame ionization detector for detection of traces of hydrocarbons in gaseous samples. The use of a laser in conjunction with flame ionization significantly increases the ratio of electronically excited CH radicals to ground electronic state CH radicals thereby increasing the signal to noise ratio during measurement, thus increasing the sensitivity of the flame ionization detection method.

In the process of the invention a pulsed laser beam with a wavelength and energy appropriate to electronically excite CH radicals in a CH radical flame zone of a flame ionization detector is directed through the flame zone thereby creating electronically excited CH radicals when ground electronic state CH radicals are present in the flame zone. Electrons created in the chemi-ionization reactions (2) are collected by an anode in an electrical circuit, thereby increasing the current flow above a steady state current present in the circuit. This increased current flow is sensed to provide a measurement of the CH radical concentration in the flame zone. The pulsed laser generates bursts of charged particles during a relatively short time interval which are synchronously detected by the sensing circuit over a similar short time interval thereby narrowing the band-width examined, thus markedly increasing the sensitivity of measurement.

Figure 1:
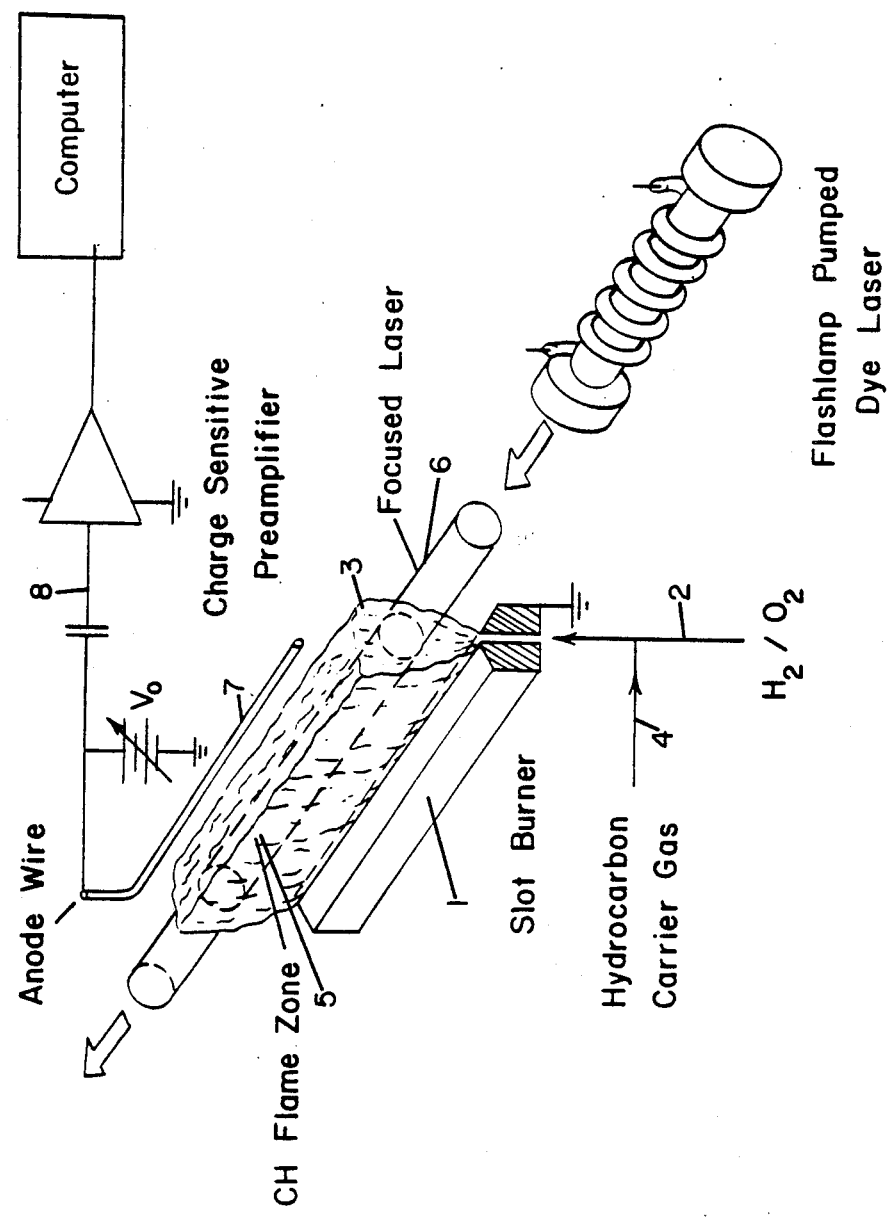
FIG. 1 is a schematic representation of apparatus adapted to create laser-enhanced ionization for the detection of CH radicals.

With reference to FIG. 1, a flame producing fuel source 2, typically comprising hydrogen and oxygen (or air) is provided through a burner head 1 to provide a flame zone 3. A controlled amount of hydrocarbon or suspected hydrocarbon containing gas is introduced into the flame zone by means of an appropriate carrier gas 4, for example an inert gas, or any other gas which is non-interfering with the radical measurements. As a significant use of the process of the invention is to quantify the effluent of a gas chromatograph, typically the carrier gas will comprise the carrier gas employed in the associated gas chromatograph. Hydrocarbons introduced into the flame zone are decomposed to form CH radicals in region of the flame zone 5. A focused laser beam 6 is directed through the CH flame zone 5 thereby creating measurably increased numbers of electronically excited CH radicals to produce chemi-electrons via reactions (2) which are collected by an anode 7 in or proximal the flame, which anode is in a signal sensing circuit 8.

Alternatively to the representation in FIG. 1 the burner head 1 can serve as the anode in the sensing circuit and the electrode 7 can be the cathode. Also chemi-ions may be detected as an alternative to the detection of chemi-electrons.

The laser employed in the process of the invention can be any laser which supplies a beam of wavelength and energy appropriate and sufficient to cause a measurable number of CH radicals to become electronically excited. The laser beam employed must be a pulsed or discontinuous laser since the short intense energy bursts create discrete highly excited CH radical concentrations which can produce periodic ionization signal peaks, which can be averaged to calculate CH radical concentration. The discrete signal peaks maximize the signal to noise ratio, thus maximizing the sensitivity of the CH radical concentration measurement.

While the flame producing burner head can be of any reasonable configuration, it is highly preferred that the burner head be a slot burner to produce an elongated flame front with the laser situated to cause the laser beam to travel essentially parallel the slot direction, thus maximizing the effective volume wherein CH radicals can effectively be excited.

While not shown in the drawings, as is well known in the art, frequently burner heads are constructed such that the gaseous components of the flammable mixture are introduced to the point of combustion through separate channels within the burner head so that a combustible mixture is not formed until just prior to the desired ignition point. In such a burner head, introduction of the carrier gas containing sample to be analyzed can be accomplished by introduction into one of the separate channels.

It is understood that the term "hydrocarbon" as employed herein encompasses any organic compound without limitation to its substituents, such as but not limited to hydroxyl, carboxyl, halogen, cyano and nitro groups and the like, including organometallic compounds, provided that such compound contains CH bonds capable of forming CH radicals in a flame zone. The preferred compounds are those which contain an abundance of such bonds, for example unsubstituted saturated and unsaturated hydrocarbons.

Further illucidating the principles of operation of the laser-enhanced flame ionization detector in FIG. 1, a pulsed laser beam traverses a hydrogen/oxygen flame in the region where CH radicals are produced by chemical reactions which result from the introduction of hydrocarbons to the flame. The laser wavelength is tuned for excitation of $CH(A^2\Delta, B^2\Sigma^-)$ radicals by absorption on either of the $CH(A^2\Delta \leftarrow X^2\pi)$ or $CH(B^2\Sigma^- \leftarrow X^2\pi)$ absorption band systems. The laser intensity and pulse duration are chosen so that a substantial fraction of the CH radicals originally present within the focal volume are induced to react via the chemi-ionization reactions (2). The electrons thus produced are detected by an ionization probe designed with characteristics defined by operating principles discussed elsewhere [Cool, *Applied Optics*, 1984, 23: 1554–1572].

The essential feature of the laser-enhanced flame ionization detector which distinguishes it from present flame ionization detectors is the enhancement in the rate of chemi-ionization which results from the laser-induced excitation of $CH(A^2\Delta, B^2\Sigma^-)$ radicals. For example, with laser enhancement, CH radicals are consumed in reactions (2) during the laser pulse time, producing a pulse of electrons. This makes possible synchronous detection, locked to the frequency and pulse duration of the exciting laser. Present flame ionization detectors are based on the detection of small steady state ionization currents. Such steady current measurements are subject to low frequency noise and drift which limit their accuracy and sensitivity. The signal averaging achievable with the repetitively pulsed laser excitation approach provides a means for substantial increases in the ratio of signal to noise, resulting in a sensitivity inherently superior to that of present steady state flame ionization detection methods. However, even the method of the invention when functioning in a steady state provides benefits in that the number of excited radicals in the steady state is increased.

IONIZATION DETECTION

The potential sensitivity of the laser-enhanced flame ionization detector is illustrated by consideration of the various parameters which define its operation. We consider one possible choice of parameters in this section; other choices are possible as is mentioned in the following section. FIG. 1 illustrates a hydrogen/oxygen flame produced by a slot burner operating at ambient atmospheric pressure within a surrounding enclosure. A pulse laser beam traverses a portion of the flame which contains CH radicals produced by chemical reactions resulting from the presence of trace quantities of a hydrocarbon gas admitted to the flame with a carrier gas flow. The approximate dimensions of the flame volume illuminated by the laser are those of a cylinder of 1 $mm^2$ cross sectional area and 10 mm length. The laser is a flashlamp pumped dye laser operating with a wavelength tuned to a suitable resonant absorption feature within the $CH(A^2\Delta \leftarrow X^2\pi)$ band system located between 4230 and 4390 Å. [Excitation of the $CH(B^2\Sigma^- \leftarrow X^2\pi)$ band system located between 3870 and 4020 Å is also feasible]. The laser has a linewidth of $\leq 1$ Å, has a pulse energy of $\geq 50$ mJ, with a pulse duration of approximately 1 microsecond. A pulse repetition rate of from 50 to 100 Hz is convenient for repetitive signal averaging.

Calculations described in the following indicate that such a laser is capable of near saturation of the $CH(A^2\Delta \leftarrow X^2\pi)$ absorption, despite the recycling of molecules back to the $X^2\pi$ state by collisional quenching, so that a large fraction of the CH radicals within the flame volume exposed to the laser are maintained in the $A^2\Delta$ electronic state during the laser pulse. Under such near saturation conditions, new $CH(A^2\Delta)$ radicals will be continuously pumped from the pool of $CH(X^2\pi)$ molecules to make up for the depletion of $CH(A^2\Delta)$ radicals by collisional quenching and chemi-ionization.

We estimate that the rate constant for the chemi-ionization reaction (2) is approximately $(8\pm6)\times 10^{-10}$ cm$^3$ molecule$^{-1}$ s$^{-1}$ for $CH(A^2\Delta)$ radicals. This value is large enough to ensure that essentially all of the CH radicals within the illuminated flame volume are ultimately removed via laser-induced chemi-ionization during the laser pulse for a density of O atoms within the flame volume exceeding about $5\times 10^{15}$ cm$^3$; such O atom densities exist within lean hydrogen/oxygen flames [Lewis, Phil. Trans. Roy. Soc., (London), 1975, A292: 45] of interest here.

The electron detection circuitry is indicated in FIG. 1. The electron charge induced at the anode wire is detected by means of a charge-sensitive preamplifier which provides a voltage output pulse with a peak amplitude which is proportional to the induced charge. The sum of the voltage pulses for a large number of pulses (ca. $10^3$) is either recorded as the output of a boxcar integrator or accumulated in the memory of a small laboratory computer.

The single pulse detection sensitivity of this arrangement is limited by the noise level of the circuitry to a value of about $10^3$ electrons per pulse, based on the specifications for the LeCroy TRA 1000 (LeCroy Research Systems of California, Palo Alto, CA) charge/current pulse preamplifier or the Amptek A225 (Amptek, Inc., Redford, MA) charge sensitive preamplifier. This sensitivity can be increased by a factor of about 30 by averaging the results of $10^3$ pulses; this results in an ultimate sensitivity limit for the detection circuitry of about 35 electrons per pulse. If the ionization efficiency of the laser enhanced flame ionization detector is about $10^{-4}$ electrons produced per carbon atom as is the case for present flame ionization detectors [see Background of the Invention], then the detection limit imposed by the circuitry is approximately $4\times 10^6/n_c$ hydrocarbon molecules, where $n_c$ is the number of carbon atoms per molecule. This sensitivity corresponds to the detection of about one hydrocarbon molecule per trillion nonhydrocarbon molecules for an atmospheric pressure flame with an illuminated flame volume of $10^{-1}$ cm$^2$ [see infra]. This sensitivity is about $10^3$ times higher than the ultimate sensitivities of present flame ionization detectors which are about $10^9$ molar, or one part per billion [see Background of the Invention]. A more complete analysis of the sensitivity of the laser-enhanced flame ionization detector is given in the following section.

THEORETICAL CONSIDERATIONS

A simplified kinetic analysis serves to illustrate the operating mechanisms of the laser-enhanced flame ionization detector. Rate equations describing the temporal variations in the CH radical and HCO$^+$ ion densities during the laser pulse, appropriate for operation at atmospheric flame pressure, are:

$$dn^+/dt = k^*Mn^* \tag{3}$$

$$dn^*/dt = (\sigma I/h\nu)(n_0 - n^*) - n^*/\tau_s - k_q Qn^* - k^*Mn^* \tag{4}$$

$$dn_0/dt = (\sigma I/h\nu)(n^* - n_0) + n^*/\tau_s + k_q Qn^* \tag{5}$$

Here $n^+$ is the density of HCO$^+$ chemi-ions produced by reactions (2), $n^*$ is the density of $CH(A^2\Delta, B^2\Sigma^-)$ radicals produced by laser absorption on the $CH(A^2\Delta \leftarrow X^2\pi)$ or $CH(B^2\Sigma^- \leftarrow X^2\pi)$ band systems, and $n_0$ is the density of $CH(X^2\pi)$ ground electronic state radicals. The effective cross section for absorption of a photon $h\nu$ between initial and final rotational states coupled within the laser linewidth is $\sigma$ [The cross section $\sigma$ is that for the $N'',J'' \to N',J'$ absorption multiplied by the fraction of the total $n_0$ population present in the $N'', J''$ state; the ratio of degeneracies for the $N'$ and $N''$ states is taken to be unity as a reasonable approximation]; $k_q$ is the bimolecular rate constant for quenching of the electronically excited $n^*$ radicals back down to ground state $n_0$ radicals in collisions with quencher molecules of density Q; $1/\tau_s$ is the spontaneous emission frequency between $n^*$ and $n_0$ radicals; $k^*M$ is the frequency of the chemi-ionization reactions (2) involving O atoms of density M.

Equations (3)–(5) are written with the assumption of rapid rotational equilibration so that Boltzmann rotational populations are maintained during the laser pulse. The solutions of these equations giving the densities at the end of a rectangular laser pulse of duration $t_p$ are:

$$n^+/n = [\lambda_1\lambda_2/(\lambda_1-\lambda_2)]\{[1-\exp(-\lambda_2 t_p)]/\lambda_2 - [1-\exp(-\lambda_1 t_p)]/\lambda_1\} \tag{6}$$

$$n^*/n = [\lambda_1 - \lambda_2/\theta(\lambda_1\lambda_2)][\exp(-\lambda_2 t_p) - \exp(-\lambda_1 t_p)] \tag{7}$$

$$n_0/n = [\lambda_1\lambda_2/\theta(\lambda_1-\lambda_2)]\{[(\theta/\lambda_2)-1]\exp(-\lambda_2 t_p) + [1-(\theta/\lambda_1)]\exp(-\lambda_1 t_p)\} \tag{8}$$

where $n = n_0 + n^* + n^+$ is the initial density of CH radicals, and $$\lambda_{1,2} = [\beta \pm \sqrt{\beta^2 - 4\theta X}]/2 \tag{9}$$

where
$\theta = k^*M$
$X = \sigma I/h\nu$
$\beta = 2X + \theta + k_q Q + 1/\tau_s$ Effective saturation of the laser absorption requires that $\sigma I/h\nu \approx k_q Q$. For the flame conditions of interest the quenching frequency greatly exceeds the frequencies of chemi-ionization and spontaneous emission, i.e., $k_p Q \gg 1/\tau_s, k^*M$. For this case $$\lambda_1 \approx \beta - \theta X/\beta \tag{10}$$

$$\lambda_2 \approx \theta X/\beta \tag{11}$$

and $$\lambda_1 \gg \lambda_2 \tag{12}$$

Moreover for this situation, $$n^+/n \approx 1 - \exp(-\lambda_2 t_p) \tag{13}$$

Equations (11) and (13) show that a high ionization efficiency requires that the laser pulse duration $t_p$ be long enough to ensure that $$k^*Mt_p \gtrsim 1 \tag{14}$$

where use has been made of the condition $\sigma I/h\nu \sim k_q Q$ for effective saturation of the absorption. This condition is easily satisfied for a pulsed laser with the parameters specified in the previous section. Other laser and flame parameters can be chosen to satisfy the condition of Equation (14), but this example makes good use of presently available lasers.

The total number of electrons $N_e$ created by chemi-ionization during the laser pulse is given by the integral of the expression for $n^+$ given in Equation (13) over the flame volume traversed by the laser pulse, $$N = \int_{-L}^{L} \int_{0}^{\infty} n^+ \, 2\pi r \, dr \, dz \tag{15}$$

When the focused laser beam may be approximated by the Gaussian beam diffraction law, its intensity is given by $$I(r,z) = I_f [A_f/A(z)] \exp[-2\pi r^2/A(z)] \tag{16}$$

where $$A(z) = A_f[1 + az^2] \tag{17}$$

where r is the radial coordinate measured from the optical axis and z is measured along the optical axis from the plane of best focus located at the center of the flame; $A_f$ is the area at the focal plane which contains 86% of the beam energy; $I_f$ is the maximum laser intensity at the focal plane; the constant "a" is defined by the geometry of the focusing lens.

An approximate solution of Equation (15), valid for the typical parameters $L=1$ cm, $aL^2=100$ cm$^{-2}$, $A_f = 2 \times 10^{-3}$ cm$^2$ and $\sigma I_f/h\nu \approx 15 k_q Q$, $t_p = 10^{-6}$ s, and $k^*M > 10^6 s^{-1}$, may be written:

$$N_e = 2nA_f L(1 + aL^2/3)[1 - \exp(-k^*Mt_p/2)] \tag{18}$$

which gives $N_e \approx 0.08$ n where n is the number density of CH radicals produced within the flame zone. If approximately $10^{-4}$ CH radicals are produced per carbon atom, then about $8 \times 10^{-6}$ n $n_c$ electrons are produced per pulse for each hydrocarbon molecule. A detection sensitivity of 35 electrons per pulse (see previous section) gives an ultimate detection sensitivity of $n = 4 \times 10^6 / n_c$ hydrocarbon molecules which is equivalent to the detection of hydrocarbons at the part-per-trillion level for typical flame conditions, as was mentioned in the previous section.

A description has been given of a laser-enhanced flame ionization detector capable of the detection of hydrocarbons at the part-per-trillion ($10^{-12}$ molar) level. This sensitivity is approximately $10^3$ times greater than the sensitivity of present flame ionization detectors. The operating principle on which the laser-enhanced flame ionization detector is based is the laser-induced reaction of CH($A^2\Delta, B^2\Sigma^-$) radicals and oxygen atoms, i.e.,

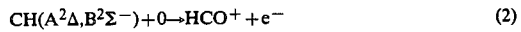

$$\tag{2}$$

A discussion of recent measurements of the rate constants for reactions (2) follows:

Introduction

The role played by electronically excited CH*($A^2\Delta$, $B^2\Sigma^-$) radicals in chemi-ionization reactions in hydrocarbon flames has been a controversial issue during the past twenty years. Conflicting evidence has been presented in an effort to determine how much, if any, of the chemi-ionization is produced by reactions involving these electronically excited CH* radicals [Fontijn et al., 10th Symposium (International) on Combustion, The Combustion Institute, 1965, p. 545; Peeters et al., 12th Symposium (International) on Combustion, The Combustion Institute, 1969, p. 437; Miller, 14th Symposium (International) on Combustion, The Combustion Institute, 1976, p. 307; Calcote, Combust. Flame, 1981, 42: 215].

The results of some simple experiments show in a conclusive and direct way that CH*($A^2\Delta$, $B^2\Sigma^-$) radicals do indeed react in hydrocarbon flames to produce significant levels of ionization. The most likely sources of the observed laser enhanced chemi-ionization are the reactions

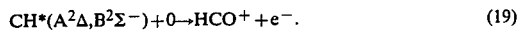

$$\tag{19}$$

The observed levels of ionization lead to estimates of the rate constants for reactions (19) at 2100° K. which are $\approx 2000$ times faster than that for the reaction

$$\tag{20}$$

Experimental

A XeCl (Xe, HCl, He) excimer-laser-pumped dye laser (Lambda-Physik FL 2002) operated with C-440 dye for the CH($A^2\Delta \leftarrow X^2\pi$)(0,0) absorption band and PBBO dye for the CH($B^2\Sigma^- \leftarrow X^2\pi$)(0,0) absorption band provided 4 ns, 1–4 mJ pulses of linearly polarized light with a linewidth of 0.5 cm$^{-1}$. The output beam of the dye laser was expanded and collimated to a 20 mm diameter beam which was focused within a low pressure flat flame (CH$_4$/O$_2$/Ar) or (C$_2$H$_4$/O$_2$/Ar) by a 150 mm focus plano-convex UV grade quartz lens. An ionization probe designed for efficient electron collection [Cool, 1984, Appl. Optics, 23: 1559] was employed for measurements of laser-enhanced chemi-ionization.

A flat flame burner with a sintered bronze porous plug burner head of 38 mm diameter was used, and a concentric shroud flow prevented recirculation of flame gases. Laser enhanced ionization could be detected for laser focal positions ranging from 3 to 16 mm above the burner surface.

Experimental Approach

Laser pulses of focused intensity $I \lesssim 2$ GW/cm$^2$ partially saturated the $A^2\Delta \leftarrow X^2\pi$(0,0) or $B^2\Sigma^- \leftarrow X^2\pi$(0,0) absorption bands for CH radicals. This established significant populations of the $A^2\Delta$ or $B^2\Sigma^-$ excited CH radicals in a short time (4 ns) compared with the radiative lifetimes (530 ns and 360 ns, respectively) [Brozozowski et al., 1976, Ap. J., 207: 414] of these excited states. Strong ionization signals resulted from the excitation of CH from the $X^2\pi$ to the $A^2\Delta$ or $B^2\Sigma^-$ states. Measurement of the number of electrons produced per laser pulse provided direct estimates of the frequency of chemi-ionization reactions involving CH($A^2\Delta$) and CH($B^2\Sigma^-$) radicals.

The experiments consisted of scanning the pulsed dye laser wavelength through the $A^2\Delta \leftarrow X^2\pi$(0,0) and $B^2\Sigma^- \leftarrow X^2\Sigma$(0,0) band systems and recording the transient laser-enhanced ionization signals. The ionization probe was designed to detect only the charge induced by the motion of the electrons on a microsecond time scale in contrast to the millisecond times associated with the motion of the more massive ions [Cool, 1984, supra]. The observed ionization signals are therefore the result of chemi-ionization reactions producing electrons which are initiated by the laser absorption.

In all of the work reported here the ionization probe was operated at a bias voltage 250 V which provided saturation of the electron collection on the "plateau" of the probe signal-voltage characteristic [Cool, 1984, supra]. A single exponential ionization signal voltage pulse with an RC=15 $\mu$sec decay time was observed; no evidence of negative ion formation was seen in the temporal behavior of the probe ionization signal [Cool, 1984, supra]. With the laser focused at a fixed position in the flame, the distance from the optical axis to the anode could be increased from the usual value of 1 mm to values as large as 12 mm with no change in the temporal shape of the ionization signal; the amplitude of the signal only decreased by 15% over this range. These results rule out significant negative ion formation (either by laser-enhanced chemi-ionization or electron attachment) and indicate that electrons were efficiently collected from the entire region of the flame illuminated by the laser.

Kinetic Considerations

Useful expressions relating the laser intensity, species densities, and laser induced ionization density are obtained from a simple rate equation analysis. At the flame pressure of 16.5 Torr, the mean time between collisions is several times longer than the laser pulse width of $t_p=4$ ns. The population of excited $CH(A^2\Delta, B^2\Sigma^-)$ molecules produced during the laser pulse can therefore be estimated by neglecting the loss of the excited molecules by reaction, collisional relaxation and radiative decay.

During the time interval $0 \leq t \leq t_p$ $$\frac{dn^*(N')}{dt} = (\sigma I/h\nu)[(g_{N'}/g_{N'})n^0(N'') - n^*(N')] \quad (21)$$

and $$\frac{dn^0(N'')}{dt} = (\sigma I/h\nu)[n^*(N') - (g_{N'}/g_{N'})n^0(N'')], \quad (22)$$

where $n^*(N')$ is the density of molecules in the $CH(A^2\Delta, B^2\Sigma^-)$ (v'=0) rotational state (N',J'); $n^0(N'')$ is the density of molecules in the $CH(X^2\pi)$ (v''=0) rotational state (N'',J''); $\sigma$ is the effective absorption cross section for the (N'←N'', J'←J'') transition over the frequency interval of the laser line of intensity I and energy $h\nu$. If the density of $CH(X^2\pi)$ molecules in the (N'',J'') rotational state at time t=0 is $X_0$, then the density of molecules $n_p^*(N')$ in the $CH(A^2\Delta, B^2\Sigma^-)$ (N'',J') state produced at the end of a rectangular laser pulse of width $t_p$ is given by the solution of Eqs. (21) and (22) as:

$$N_p^*(N'')=X_0(1+g_{N'}/g_{N'})^{-1}[1-\exp(-\beta I)] \quad (23)$$

where $$\beta = \sigma t_p (1+g_{N'}/g_{N'})/h\nu.$$

Following the laser pulse, $$dn^+/dt = k^*Mn^* \quad (24)$$

$$dn^*/dt = -n^*(k^*M + k_qQ + 1/\tau) \quad (25)$$

where $$n^* = \sum_{N'} n^*(N')$$

is the total density of molecules in the $CH(A^2\Delta, B^2\Sigma^-)$ (v'=0) state (which are subject to rotational relaxation following the laser pulse); $n^+$ is the density of ions produced by the chemi-ionization reactions $$n^* + M_i \xrightarrow{k_i} n^+ + e^- + \text{(products)} \quad (26)$$

and $k^*M = \Sigma_i k_i M_i$ is the total frequency of the chemi-ionization reactions (26); $k_qQ$ is the total frequency for bimolecular quenching processes with the species i of densities $Q_i$ and $1/\tau$ is the frequency of decay of the $CH(A^2\Delta, B^2\Sigma^-)$ molecules by spontaneous emission and predissociation. The dependence of the chemi-ionization, quenching, and spontaneous decay processes on the rotational quantum number N' is neglected as a reasonable first approximation. Solution of Eqs. (24) and (25) with the initial conditions $n^* = n_p^*(N')$ and $n^+ = 0$ gives for the total density of laser induced chemi-ions, $$n_f^+ = n^+(t \approx \infty) = n_p^*(N')k^*M/(k^*M + k_qQ + 1/\tau) \quad (27)$$

The total number of electrons $N_e$ created by chemi-ionization (assuming equal densities of electrons and chemi-ions) is given by the integral of $n_f^+$ over the flame volume traversed by the laser pulse, $$N_e = \int_{-L}^{L} \int_0^\infty n_f^+ 2\pi r \, dr \, dz \quad (28)$$

where r is the radial coordinate measured from the optical axis and z is measured along the optical axis from the plane of best focus located at the center of the flame. The axial variation of beam spot size was determined by direct photographic measurement [Cool, 1984, supra]. For the 150 mm focal length lens used in these experiments $\approx 90\%$ of the beam energy was contained within the cross sectional area $$A(z) = A_f[1+az^2] \quad (29)$$

Here $a=94$ cm$^{-2}$ and $A_f=1.9\times 10^{-4}$ cm$^2$. The radial dependence of beam intensity is assumed to approximate the Gaussian beam diffraction law:

$$I(r,z) = I_f[A_f/A(z)] \exp[-2\pi r^2/A(z)] \quad (30)$$

The use of Eqs. (23), (27)-(30) yields the expressions:

$$N_e = X_0 G A_f L k^*M(k^*M + k_qQ + 1/\tau)^{-1} \theta, \quad (31)$$

where $G = 2(1+g_{N'}/g_{N'})^{-1}$ and $\theta$ is the integral $$\theta = \int_0^1 (1 + aL^2u^2)[E_1(\alpha) + \ln(\alpha) + \gamma] \, du \quad (32)$$

with $\alpha \equiv \beta I_f(1+aL^2u^2)^{-1}$; $E_1(\alpha)$ is the exponential integral [Abramowitz et al., *Handbook of Mathematical Functions*, (Dover Publications, Inc., NY, 1970) p. 228].

Two limiting forms of Eqs. (31) and (32) are of interest. When $I_f$ is very large we have $$N_e(I_f \text{ large}) \approx X_o G A_f L (aL^2/3)[\ln(\beta I_f/aL^2)+1.25]k^*M[k^*M+k_qQ+1/\tau]^{-1} \quad (31a)$$

for the present experiments where $aL^2 >> 1$. for small $I_f$ $$N_e(I_f \text{ small}) \approx X_o G A_f L \beta I_f k^* M[k^*M+k_qQ+1/\tau]^{-1}. \quad (31b)$$

Experimental Results

Figure 2:
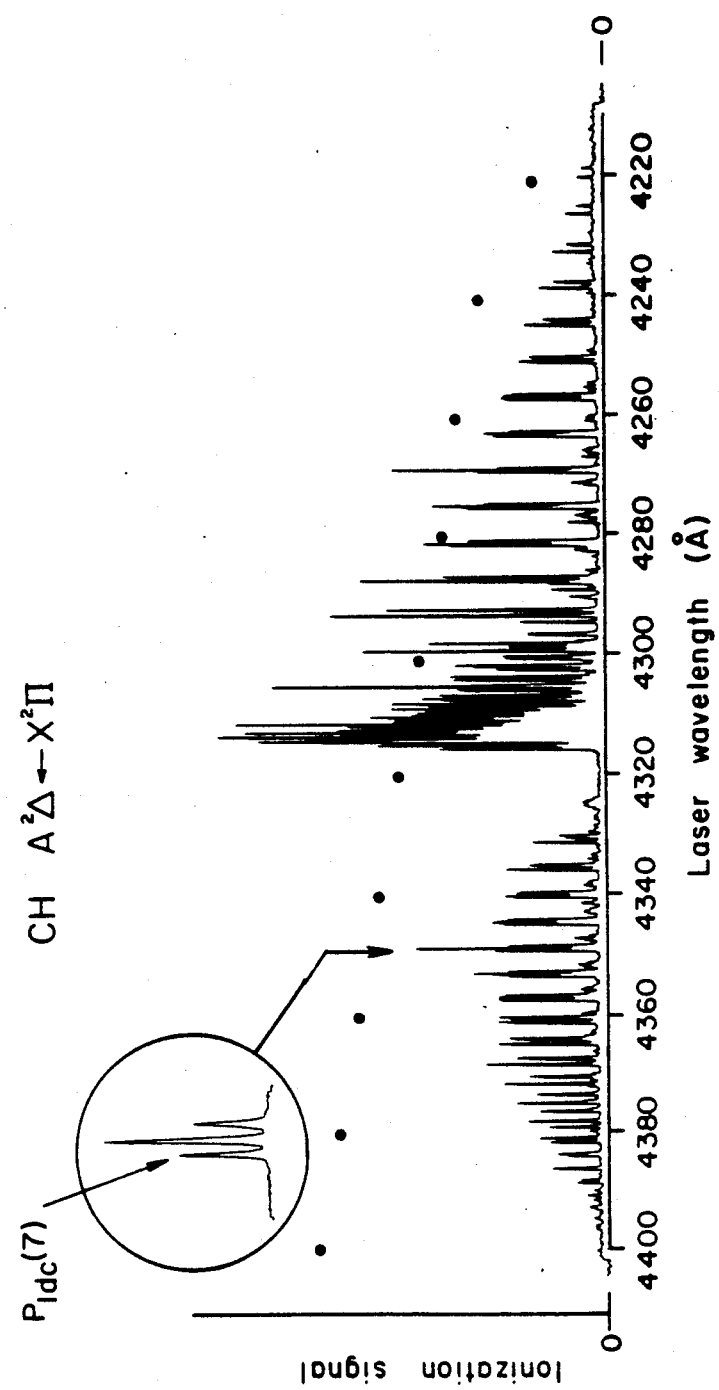
FIG. 2 is the ionization spectrum for the $CH(A^2\Delta \leftarrow X^2\pi)(0,0)$ band system obtained with C-440 dye. For a $CH_4/O_2/Ar$ (1/2.26/0.83) $\phi = 0.88$ flame at a pressure of 16.5 Torr. The solid points indicate the variation in laser pulse energy with wavelength; the pulse energy was 2 mJ at 4350 Å. The arrow points to the peak corresponding to the $P_{ldc}(7)$ transition near 4359 Å. The spectra of FIGS. 2 and 3 were obtained with the laser focus 8.8 mm above the burner (see FIG. 4) and 1 mm from the probe anode surface.
Figure 3:
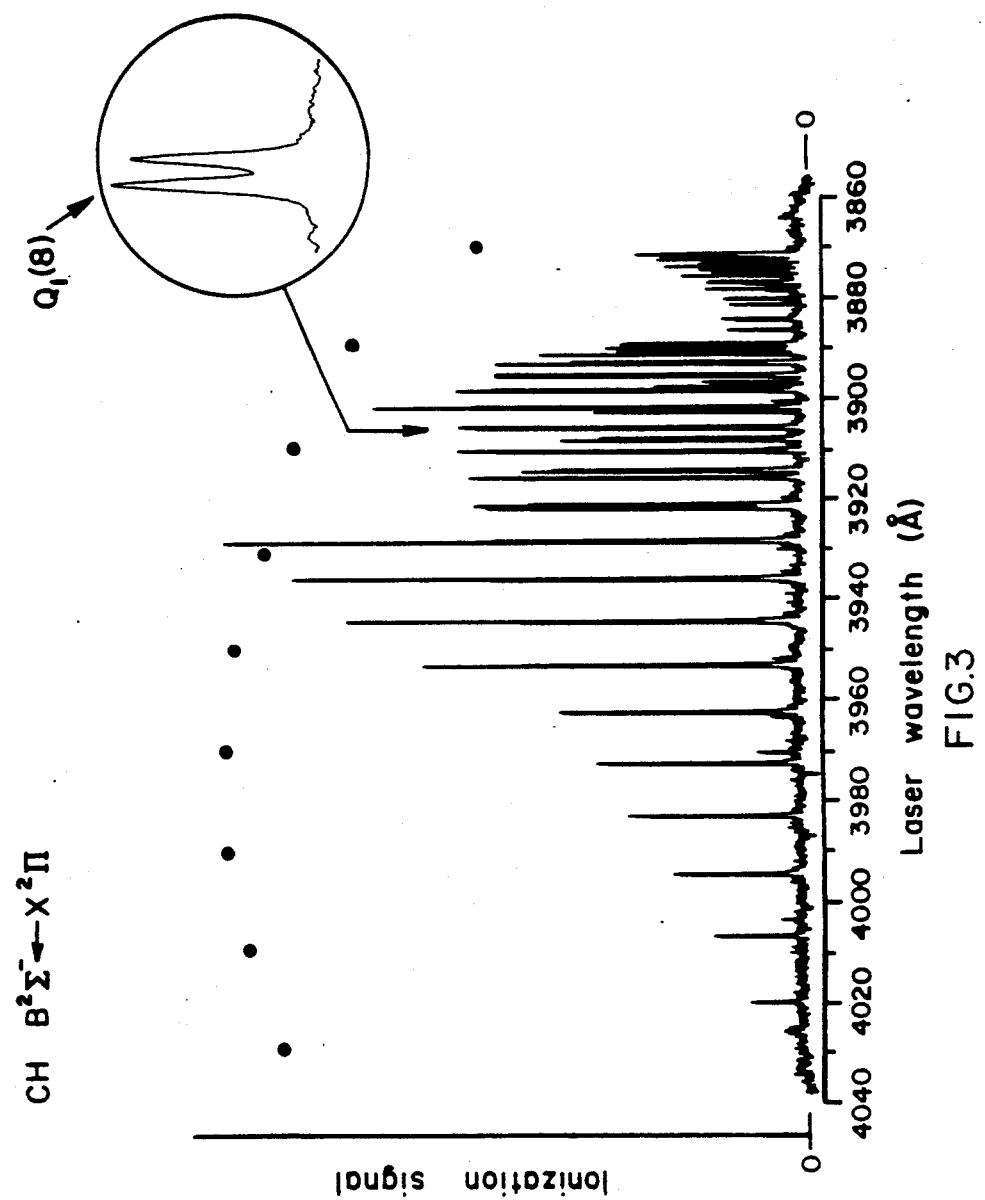
FIG. 3 is the ionization spectrum for the $CH(B^2\Sigma^- \leftarrow X^2\pi)(0,0)$ band system obtained with PBBO dye. For a $CH_4/O_2/Ar$ (1/2.26/0.83) $\phi = 0.88$ flame at a pressure of 16.5 Torr. The solid points indicate the variation in laser pulse energy with wavelength; the pulse energy was 2 mJ at 3900 Å. The arrow indicates the $Q_1(8)$ transition near 3907 Å used for the present measurements (FIG. 5). The resolved $Q_1(8)$ transition exhibits an AC Stark broadened FWHM of $\approx 1$ cm$^{-1}$; under low intensity excitation the observed linewidth decreases to the 0.5 cm$^{-1}$ laser linewidth.

Ionization spectra of the $CH(A^2\Delta \leftarrow X^2\pi)(0,0)$ and $CH(B^2\Sigma^- \leftarrow X^2\pi)(0,0)$ band systems obtained by scanning the dye laser wavelength are given in FIGS. 2 and 3. Spectra of similar appearance were obtained for both $CH_4/O_2/A_r$ ((1/2.26/0.83) $\phi=0.88$ and $C_2H_4/O_2/Ar$ (1/3.65/4.2) $\phi=0.80$ flames operated at a pressure of 16.5 Torr. The ionization spectra exhibited a Boltzmann distribution among the rotational states. A flame temperature of $2100\pm100K$ was obtained from the P-branch transitions of the $A^2\Delta \leftarrow X^2\pi$ band system for both flames.

Figure 4:
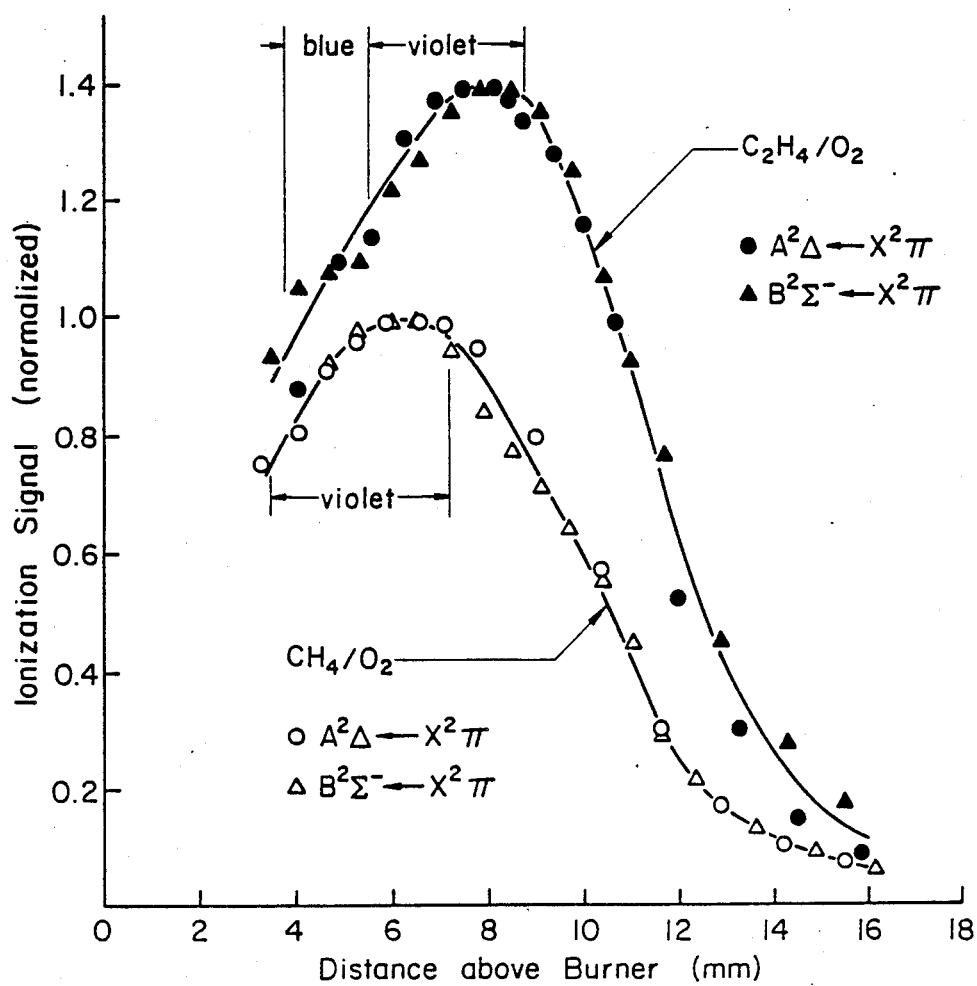
FIG. 4 shows the variation of the ionization signal $N_e$ with distance of the laser focus above the burner for $CH_4/O_2/Ar$ (1/2.26/0.83) $\phi = 0.88$ and $C_2H_4/O_2/Ar$ (1/3.65/4.2) $\phi = 0.80$ flames at 16.5 Torr. Data for 2 mJ laser pulses for both the (A$\leftarrow$X) $P_{ldc}(7)$ and (B$\leftarrow$X) $Q_1(8)$ transitions are indicated. The peak of the upper curve ($C_2H_4$) corresponds to $N_e \approx 3 \times 10^7$; the peak of the lower ($CH_4$) curve represents $N_e \approx 2.1 \times 10^7$; both transitions gave nearly equal peak $N_e$ values. The laser focus was located 1 mm from the probe anode surface for these data. The boundaries of the luminous flame zones are indicated.

The variations in ionization signal with distance between the burner surface and the laser focus for both band systems and both flames are shown in FIG. 4. Within experimental error ($\pm15\%$) the ratio of ionization signals obtained for the $C_2H_4/O_2/Ar$ and $CH_4/O_2/Ar$ flames was 1.4 for either band system. The signals obtained with the two band systems have been normalized to the same peak values for each flame in FIG. 4; as it happened, the actual signals for the $A \leftarrow X$ and $B \leftarrow X$ transitions chosen for the data of FIG. 4 were nearly equal (to within 10%) for the same laser pulse energy. The flame conditions for FIGS. 2-4 were chosen to match closely the conditions for which Peeters and Vinckier [Peeters et al., 15th Symposium (International) on Combustion, The Combustion Institute, 1975, p. 969] have made extensive measurements of flame radical profiles. The profiles of CH and O reported in Peeters et al., 1975, supra, for the two flames provide profiles of the product of CH and O densities which are narrower than the ionization signal profiles of FIG. 4, but have the same qualitative appearance with peak values located within the luminous flame zone near its outer edge, in agreement with the data of FIG. 4. The 40% larger signals obtained from the $C_2H_4/O_2/Ar$ flame are consistent with the larger (x2) product of CH and O concentrations for this flame.

Figure 5:
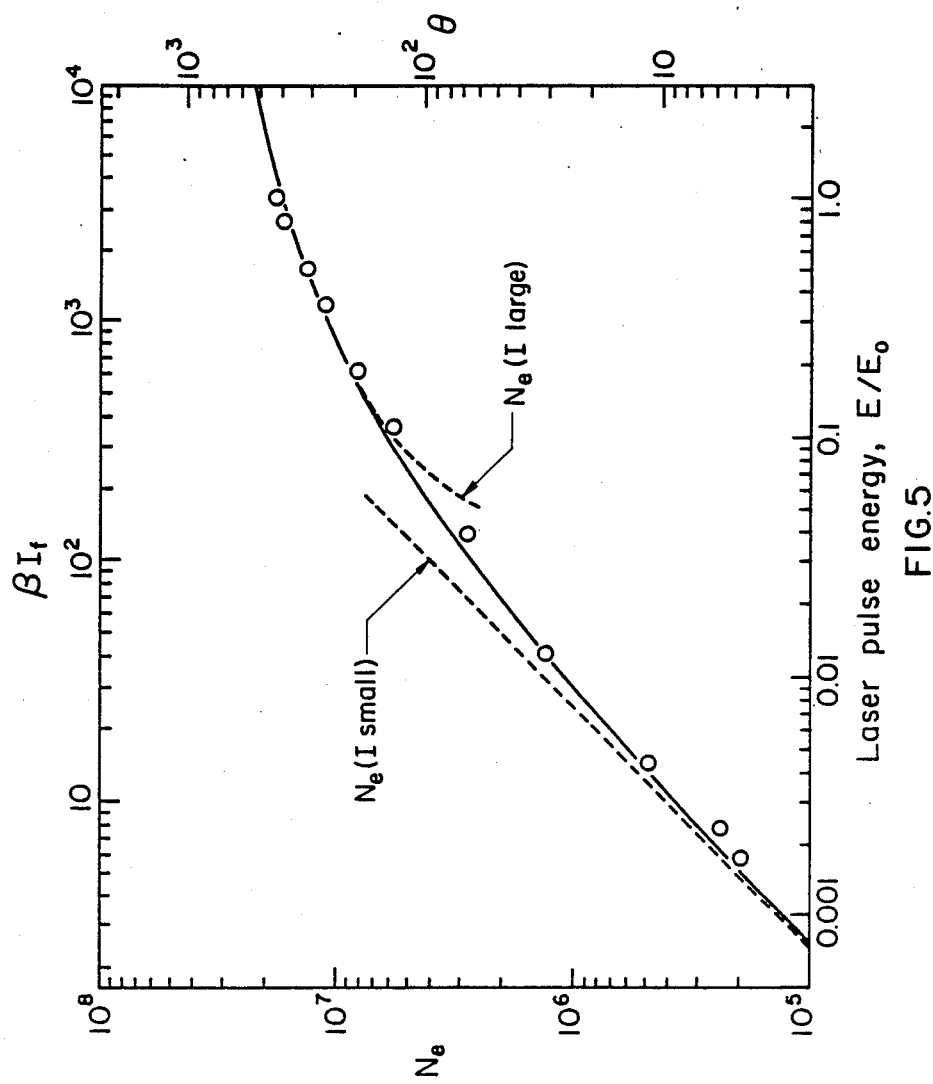
FIG. 5 shows the variation of the ionization signal $N_e$ with laser pulse energy for a $CH_4/O_2/Ar$ (1/2.26/0.83) $\phi = 0.88$ flame at 16.5 Torr. The total laser pulse energy was 2 mJ; $E_0 = 1.8$ mJ was contained within the area $A_f = 1.9 \times 10^{-4}$ cm$^2$ at the focal plane. The data are for the $Q_1(8)$ transition of the $B^2\Sigma^- \leftarrow X^2\pi$ band system taken with the laser focus 8.8 mm above the burner (see FIG. 4) and 1 mm from the probe anode surface. Also shown are theoretical curves of the variation of $\theta$ with $\beta I_f$ which have been fit to the data.

The variation of laser induced ionization with laser pulse energy (intensity) for the $CH(B^2\Sigma^- \leftarrow X^2\pi)$ transition is displayed in FIG. 5. The dye laser was set for the $Q_1(8)$ rotational line near 3907 Å indicated in FIG. 3. These data were obtained with the use of neutral density attenuators placed across the expanded and collimated laser bean [Cool, 1984, supra]. The electron density $N_e$ data of FIG. 5 represent the number of electrons measured by the ionization probe $(Q_t^-/e)$ [Cool, 1984, supra] multiplied by a factor of 1.7 to account for probe collection efficiency effects $([V^+ - V(x)]/V_o=0.7; \zeta=0.85)$ [Cool, 1984, supra].

The solid curve shown with the data of FIG. 5 shows the dependence of $N_e$ and $\theta$ on $\beta I_f$ and on the laser pulse energy E for the parameters of the present experiments. These parameters include the measured values $aL^2=340$, $A_f=1.9\times10^{-4}$ cm$^2$, $L=1.9$ cm and $E_o=1.8$ mJ. The fitting of FIG. 5 results from the choice of $\sigma/h\nu=174$ cm$^2$/J. (This value is an order of magnitude less than indicated by a direct calculation for a Doppler broadened $Q_1(8)$ transition and a laser linewidth of 1 cm$^{-1}$.) These parameters give a theoretical curve with a shape which correctly matches the experimental data; a matching of the computed and measured values of $N_e$ along the vertical axis depends on the additional parameters $X_o$ and $k^*M/(k^*M+k_qQ+1/\tau)$. The data of FIG. 5 were taken 8.8 mm above the burner, almost 2 mm outside of the luminous reaction zone (see FIG. 4). At this position the CH density should be about $5\times10^{11}$ cm$^{-3}$ [Peeters et al., 1975, supra] of which $X_o=1.8\times10^{10}$ cm$^{-3}$ would be in the (v''=0, N''=8, J''=8½) lower state for the $Q_1(8)$ transition of the $B^2\Sigma^- \leftarrow X^2\pi(0,0)$ system at 2100° K. Use of this value of $X_o$ requires that $k^*M/(k^*M+k_qQ+1/\tau)=0.0067$ for $CH(B^2\Sigma^-)$ radicals to accomplish the fitting of FIG. 5.

A similar determination for $CH(A^2\Delta)$ radicals of $k^*M/(k^*M+kQ+1/\tau)=0.0144$ results from a fitting of $N_e$ vs. E data for the $P_{ldc}(7)$ line of the $A^2\Delta \leftarrow X^2\pi$ system. For this case $N_e=1.7\times10^7$ when $E_o=1.8$ mJ; $aL^2=340$, $A_f=1.9\times10^{-4}$ cm$^2$, $L=1.9$ cm, and $\sigma/h\nu$ was chosen to be 110 cm$^2$/J. The value of $X_o$ is $9.6\times10^9$ cm$^{-3}$ for the resolved $\Lambda$-splitting component $P_{ldc}(7)$ (see FIG. 2).

Discussion

The present flames were chosen for study as a means to distinguish between the chemi-ionization processes (19) and the reactions

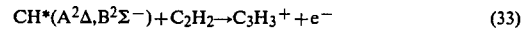

$$CH^*(A^2\Delta,B^2\Sigma^-)+C_2H_2\rightarrow C_3H_3^++e^- \quad (33)$$

which have been proposed as a possible source of chemi-ionization in hydrocarbon flames [Fontijn et al., 10th Symposium (International) on Combustion, The Combustion Institute, 1965, P. 545; Peeters et al., 12th Symposium (International on Combustion, The Combustion Institute, 1969, p. 437; Miller, 14th Symposium (International) on Combustion, The Combustion Institute, 1973, p. 307; Calcote, 1981, Combust. Flame, 42: 215]. Peeters and Vinckier [Peeters et al., 1975, supra] report large concentrations ($\approx2\%$) of $C_2H_2$ in the flame front of a $C_2H_4/O_2/Ar$ ($\phi=1.06$) flame. In contrast the concentration of $C_2H_2$ in the $CH_4/O_2/Ar$ flame should not exceed a few ppm [Peeters et al., 14th Symposium (International) on Combustion, The Combustion Institute, 1973, p. 133]. The observed levels of ionization enhancement require that the species reacting with $CH^*(A^2\Delta, B^2\Sigma^-)$ radicals be present in substantial concentrations ($>1\%$). This rules out the participation of reaction (33) in the $CH_4/O_2/Ar$ flame, which leaves reaction (19) as the only presently suggested mechanism which could account for the enhanced chemi-ionization in this flame. Moreover, as mentioned above, the relative ionization enhancements for the two flames are in rough agreement with the relative values for the product of CH and O concentrations [Peeters et al., 1975, supra]. It therefore seems likely that reactions (19) account for the ionization enhancement in both flames.

If this is the case, the values for $k^*M/(k^*M+k_qQ+1/\tau)$ determined in above permit estimates of the rate constants $k^*$ for reactions (19). The density of O atoms at the flame position for the measurements discussed above should be about $M=7.6\times10^{14}$ cm$^{-3}$ [Peeters et al., 1975, supra] and the values of $\tau$ are 530 ns and 360 ns for the $A^2\Delta(v'=0)$ and $B^2\Sigma^-$ (v'=0) states, respectively [Brozozowski et al., 1976, supra]. Much uncertainty presently exists concerning the collisional quenching constants $k_{qi}$. Measurements for quenching of $CH(A^2\Delta)$ by several species at room temperature have been reported [Nokes et al., 1983, *Chem. Phys. Letters*, 99: 491]. A value for the quenching frequency $k_qQ$ of $3\times 10^9$ sec$^{-1}$ has been estimated for the $A^2\Delta$ (v'=0) state for an atmospheric pressure $C_2H_2/O_2$ flame [Bonczyk et al., 1979, *Combust. Flame*, 34: 253]. Values of $k_qQ=2\times 10^9$ sec$^{-1}$ for CN($B^2\Sigma$) and OH-($A^2\Sigma^+$) radicals in atmospheric pressure flames have also been cited [Bonczyk et al., 1979, *Combust. Flame*, 34: 253; Cottereau et al., *Laser Probes for Combustion Diagnostics*, D. R. Crosley, Ed., American Chemical Society Symposium Series No. 134 (American Chemical Society, Washington, D.C., 1980) p. 131]. In the absence of better information the value $k_qQ\approx(4\pm3)\times 10^7$ sec$^{-1}$ for CH($A^2\Delta$) may be a reasonable estimate for the present low pressure ($CH_4/O_2/Ar$) flame; the values of $k_qQ$ for the CH($B^2\Sigma^-$) radicals might be expected to lie at the upper limit of this range because of a much lower bond energy and an anticipated greater chemical reactivity. These considerations suggest values of $k^*=(8\pm6)\times10^{-10}$ cm$^3$ molecule$^{-1}$ s$^{-1}$ for CH($A^2\Delta$) and $(5\pm3)\times10^{-10}$ cm$^{-3}$ molecule$^{-1}$ s$^{-1}$ for CH($B^2\Sigma^-$) radicals. These estimates place the rate constants for reaction (19) approximately 2000 times larger than the previously measured value of $2.8\times10^{-13}$ cm$^{-3}$ molecule$^{-1}$ s$^{-1}$ for reaction (20) for the 2000°–2400° K. range [Peeters et al., 1973, supra].

Within hydrocarbon flame fronts the concentrations of CH*($A^2\Delta$, $B^2\Sigma^-$) radicals can exceed thermal equilibrium populations by several orders of magnitude [Gaydon, *The Spectroscopy of Flames*, (Chapman and Hall, London, 1974) p. 187]; in these regions the chemi-ionization attributable to reactions (19) may approach that of reaction (20). For thermal equilibrium conditions at typical flame temperatures of 2400° K. the contributions of reactions (19) would be negligible compared to that of reaction (20).

It may be useful to calibrate any apparatus within the scope of this invention against known quantities of various organic compounds under varied conditions to note the particular effect if any of that apparatus on the equal per carbon response, the collection of ions and carrier gas effects, for example as discussed by Blades, supra.

It should be understood that the invention can be practiced by those skilled in the art in ways other than exemplied within the scope of the claims.

We claim:

1. In a method of flame ionization detection wherein a chemical compound or mixture thereof capable of generating CH radicals is ionized in a non-interfering flame zone to generate charged particles and the charged particles sensed in an electrical circuit to determine the amount of chemical compound or compounds present in the flame zone, the improvement which comprises:

Periodically electronically exciting the CH radicals within the ionizing region of the flame zone to either the $A^2\Delta$ or $B^2\Sigma^-$ state with a pulsed or discontinuous laser beam having a light wavelength adapted to enhance the chemi-ionization reaction, and sensing the charged particles created during the laser beam excitation periods, thereby increasing the desired signal-to-noise ratio read by the sensing means.

2. A method as in claim 1 wherein the laser beam is a pulsed laser beam and the charged particle caused signal generated when CH radical producing compounds are present demonstrates peaks which correlate with the laser beam pulse periods.

3. A method as in claim 1 wherein the flame zone comprises a flame front along an elongated axis and the laser beam passes through the flame zone substantially parallel to the elongated axis of the flame zone.

4. A method as in claim 1 wherein the flame zone comprises a hydrogen-oxygen flame.

5. A method as in claim 1 wherein the compound or a mixture of compounds being detected comprises the effluent from a gas chromatograph.

6. An apparatus for flame ionization detection of a CH radical producing chemical compound which comprises:
   means for creating an ionizing flame zone;
   means for delivering a gaseous sample into said flame zone;
   means for passing a pulsed or discontinuous laser beam through said flame zone to electronically excite CH radicals when present;
   means for sensing chemi-ionization caused by the excited CH radicals created by the laser beam in said flame zone.

7. The apparatus as in claim 6 wherein the laser beam is a pulsed laser beam.

* * * * *